(12) United States Patent
Freson et al.

(10) Patent No.: US 7,615,219 B2
(45) Date of Patent: Nov. 10, 2009

(54) INHIBITION OF PACAP SIGNALLING FOR THE PREVENTION AND TREATMENT OF THROMBOCYTOPENIA

(75) Inventors: Kathleen Freson, Heverlee (BE); Chris Van Geet, Nieuwrode (BE); Marc Hoylaerts, Kessel-Lo (BE)

(73) Assignee: Life Sciences Research Partners VZW, Leuven (BE)

( * ) Notice: Subject to any disclaimer, the term of this patent is extended or adjusted under 35 U.S.C. 154(b) by 391 days.

(21) Appl. No.: 10/542,238

(22) PCT Filed: Jan. 16, 2004

(86) PCT No.: PCT/EP2004/001209

§ 371 (c)(1),
(2), (4) Date: Jul. 15, 2005

(87) PCT Pub. No.: WO2004/062684

PCT Pub. Date: Jul. 29, 2004

(65) Prior Publication Data

US 2006/0062785 A1     Mar. 23, 2006

(30) Foreign Application Priority Data

Jan. 16, 2003  (GB) ................... 0300934.7
Apr. 3, 2003   (GB) ................... 0307667.6
Apr. 3, 2003   (GB) ................... 0310037.7

(51) Int. Cl.
    *A61K 39/395*   (2006.01)
(52) U.S. Cl. .............. 424/139.1; 424/130.1; 424/133.1; 424/141.1; 424/153.1
(58) Field of Classification Search ............... None
    See application file for complete search history.

(56) References Cited

U.S. PATENT DOCUMENTS

| 5,486,472 A * | 1/1996 | Suzuki et al. ............... 435/336 |
| 6,242,563 B1 | 6/2001 | Dong |
| 2002/0182729 A1* | 12/2002 | DiCicco-Bloom et al. .. 435/368 |

FOREIGN PATENT DOCUMENTS

| WO | WO 00/05260 | 2/2000 |
| WO | WO 00/23096 | 4/2000 |
| WO | WO 01/23420 | 4/2001 |
| WO | WO 2004/062684 | 7/2004 |
| WO | WO 2004/062684 A2 | 7/2004 |

OTHER PUBLICATIONS

Kobayashi et al., Leuk Lymphoma, 1994, 15:45-49.*
Bibel et al., Genes and Development, 2000, 14:2919-2937.*
Sherwood et al., Endocrine Reviews, 2000, 21:619-670.*
Takizawa et al., Experimental Hematology, 2008, 36:897-906.*
Dhanjal et al., Blood, 2007, 109:4237-4244.*

Freson et al., "PACAP and Its Receptor VPAC1 Regulate Megakaryocyte Maturation: Therapeutic Implications," *Blood* 111(4):1885-1893 (2008).
Freson et al., "VPAC1 Receptor-Mediated Regulation of Megakaryopoiesis," *Blood* 104(11):210A (2004). Abstract 735.
Goetzl et al., "Specific Recognition of the Human Neuroendocrine Receptor for Vasoactive Intestinal Peptide by Anti-Peptide Antibodies," *Mol. Cell. Neurosci.* 5(2):145-152 (1994).
Communication mailed in connection with EP 07012752.7-1222 on Mar. 28, 2008.
Cox et al.,"VIP Elevates Platelet Cyclic AMP (cAMP) Levels and Inhibits In Vitro Platelet Activation Induced By Platelet-Activating Factor (PAF)," *Peptides*, 5:325-328 (1984).
Freson et al., "The Pituitary Adenylate Cyclase-Activating Polypeptide Is a Physiological Inhibitor of Platelet Activation," *The Journal of Clinical Investigation*, 113:905-912 (2004).
International Search Report (PCT/EP2004/001209).
Written Opinion of ISA (PCT/EP2004/001209).
International Preliminary Report on Patentability (PCT/EP2004/001209).
Ashur-Fabian et al., "Identification of VIP/PACAP Receptors on Rat Astrocytes Using Antisense Oligodeoxynucleotides," *J. Mol. Neurosci.* 9(3):211-222 (1997).
Bibel and Barde, "Neurotrophins: Key Regulators of Cell Fate and Cell Shape in the Vertebrate Nervous System," *Genes Dev* 14(23):2919-2937 (2000).
Busto et al., "Evidence for Multiple Rat $VPAC_1$ Receptor States with Different Affinities for Agonists," *Cell Signal.* 11(9):691-696 (1999).
Cox et al., "VIP Elevates Platelet Cyclic AMP (cAMP) Levels and Inhibits In Vitro Platelet Activation Induced by Platelet-Activating Factor (PAF)," *Peptides* 5(2):325-328 (1984).
Dhanjal et al., "A Novel Role for PECAM-1 in Megakaryocytokinesis and Recovery of Platelet Counts in Thrombocytopenic Mice," *Blood* 109(10):4237-4244 (2007).
Freson et al., "VPAC1 Receptor-Mediated Regulation of Megakaryopoiesis," *Blood* (ASH Annual Meeting Abstracts) 104:Abstract 735 (2004).
Freson et al., "The Pituitary Adenylate Cyclase-Activating Polypeptide Is a Physiological Inhibitor of Platelet Activation," *J. Clin. Invest.* 113(6):905-912 (2004).
Kobayashi et al., "Interleukin 11," *Leuk. Lymphoma* 15(1-2):45-49 (1994).
Sherwood et al., "The Origin and Function of the Pituitary Adenylate Cyclase-Activating Polypeptide (PACAP)/Glucagon Superfamily," *Endocrine Reviews* 21(6):619-670 (2000).
Shima et al., "Characterization of VIP- and Helodermin-Preferring Receptors on Rat Platelets," *Regulatory Peptides* 63(2-3):99-103 (1996).

(Continued)

*Primary Examiner*—Michael Szperka
(74) *Attorney, Agent, or Firm*—Clark & Elbing LLP

(57) ABSTRACT

The present invention discloses the use of inhibitors and/or antagonists of PACAP signalling for the manufacture of a medicament for the prevention or treatment of decreased blood platelet numbers (thrombocytopenia).

7 Claims, 8 Drawing Sheets

OTHER PUBLICATIONS

Takizawa et al., "Growth and Maturation of Megakaryocytes Is Regulated by Lnk/Sh2b3 Adaptor Protein Through Crosstalk Between Cytokine- and Integrin-Mediated Signals," *Exp. Hematol.* 36(7):897-906 (2008).

Tams et al., "Creation of a Selective Antagonist and Agonist of the Rat $VPAC_1$ Receptor Using a Combinatorial Approach with Vasoactive Intestinal Peptide 6-23 as Template," *Mol. Pharmacol.* 58(5):1035-1041 (2000).

* cited by examiner

A

B

C

SEQUENCE LISTING

```
<160> NUMBER OF SEQ ID NOS: 9

<210> SEQ ID NO 1
<211> LENGTH: 38
<212> TYPE: PRT
<213> ORGANISM: Homo sapiens

<400> SEQUENCE: 1

His Ser Asp Gly Ile Phe Thr Asp Ser Tyr Ser Arg Tyr Arg Lys Gln
 1               5                  10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 2
<211> LENGTH: 27
<212> TYPE: PRT
<213> ORGANISM: Homo sapiens

<400> SEQUENCE: 2

His Ser Asp Gly Ile Phe Thr Asp Ser Tyr Ser Arg Tyr Arg Lys Gln
 1               5                  10                  15

Met Ala Val Lys Lys Tyr Leu Ala Ala Val Leu
            20                  25

<210> SEQ ID NO 3
<211> LENGTH: 31
<212> TYPE: DNA
<213> ORGANISM: Homo sapiens

<400> SEQUENCE: 3
gtagccgctc gaggatctgc tacaagtatg c                              31

<210> SEQ ID NO 4
<211> LENGTH: 31
<212> TYPE: DNA
<213> ORGANISM: Homo sapiens

<400> SEQUENCE: 4
gttagccgaa ttcagttcaa ggtctggcta g                              31

<210> SEQ ID NO 5
<211> LENGTH: 22
```

```
<212> TYPE: DNA
<213> ORGANISM: Homo sapiens

<400> SEQUENCE: 5
tggccacatc acagcattca ag                                              22

<210> SEQ ID NO 6
<211> LENGTH: 21
<212> TYPE: DNA
<213> ORGANISM: Homo sapiens

<400> SEQUENCE: 6
accaactggg acgacatgga g                                               21

<210> SEQ ID NO 7
<211> LENGTH: 24
<212> TYPE: DNA
<213> ORGANISM: Homo sapiens

<400> SEQUENCE: 7
cgtgaggatc ttcatgaggt agtc                                            24

<210> SEQ ID NO 8
<211> LENGTH: 20
<212> TYPE: DNA
<213> ORGANISM: Homo sapiens

<400> SEQUENCE: 8
gaagcacctg cagtcgctcg                                                 20

<210> SEQ ID NO 9
<211> LENGTH: 17
<212> TYPE: DNA
<213> ORGANISM: Homo sapiens

<400> SEQUENCE: 9
tgtatacaca gggtagc                                                    17
```

US 7,615,219 B2

INHIBITION OF PACAP SIGNALLING FOR THE PREVENTION AND TREATMENT OF THROMBOCYTOPENIA

CROSS REFERENCE TO RELATED APPLICATIONS

This application is the U.S. National Stage of International Application No. PCT/EP2004/001209, filed Jan. 16, 2004, which, in turn, claims the benefit of GB Application Nos. 0300934.7, 0307667.6, and 0310037.7 filed Jan. 16, 2003, Apr. 3, 2003 and Apr. 3, 2003 respectively.

FIELD OF THE INVENTION

This invention relates to compounds useful in the control of the primary haemostasis and the modulation of platelet number, as well as methods of use of these compounds.

BACKGROUND OF THE INVENTION

The initial response to interruption of continuity of a blood vessel is defined as primary haemostasis. Platelets play a major role in the pathophysiology of primary haemostasis. The clinical importance of platelets first became obvious when thrombocytopenic patients, who later on were diagnosed as having immune mediated thrombocytopenia (ITP), had thrombocytopenic purpura. Platelets participate in haemostasis by sealing vascular injuries and by fostering the process of blood coagulation. Not only the number of the platelets is important (thrombocytopenia for whatever reason) but also their intrinsic function upon activation: change in platelet shape, adhesion, aggregation and secretion are prerequisites for normal haemostasis. Congenital or acquired disorders interfering with one of the platelet functions can lead to mild to even severe bleeding problems.

Prevention and treatment of bleeding in patients with thrombocytopenia or thrombocytopathia is therefore based on platelet transfusion or medication interfering with platelet number and/or function.

Platelets also play a role in the development of arterial thrombosis. Disruption of the endothelial cell lining of the vessels exposes adhesive proteins within the subendothelial matrix, leading to platelet attachment. Thereafter, platelet spreading, as well as platelet secretion occurs. The secretion of the content of platelet granules can stimulate circulating platelets to acquire new adhesive properties. Finally, stimulated platelets interact with each other during platelet aggregation and a platelet rich thrombus is formed, which can compromise the patency of blood vessels. Furthermore activated platelets accelerate the rate of activation of coagulation proteins. Phospholipids on the platelet surface facilitate thrombin generation and fibrin strand formation.

Arterial and venous thrombosis and their complications including ischemic stroke, acute myocardial infarction and venous thromboembolism, represent the major cause of morbidity and mortality in developed countries.

Prevention and treatment of thrombosis are therefore based on administration of antiplatelet drugs, anticoagulants or thrombolytic therapy or combinations thereof.

The pituitary Adenylyl Cyclase Activating Peptide (PACAP 1-38) is a 38-amino acid peptide that was first isolated from ovine hypothalamic extracts on the basis of its ability to stimulate cAMP formation in anterior pituitary cells [Miyata A. et al., (1989) *Biochem Biophys Res Commun* 164, 567-574; Vaudry D. et al. (2000) *Pharm Rev* 52, 269-324]. PACAP is a member of the Vasoactive Intestinal Polypeptide (VIP)—glucagon-growth hormone releasing factor-secretin superfamily. Its role in biology is probably crucial, since the sequence of PACAP is highly conserved during the evolution from protochordate to mammals. PACAP is widely expressed and occurs in the central and peripheral nervous system, the urogenital system, the gastrointestinal tract, and in several endocrine glands. PACAP receptors are also widely distributed (Vaudray et al. cited supra). Two classes of PACAP binding sites have been characterized based on their relative affinities for PACAP and VIP: type I binding sites with high affinity for PACAP (Kd=0.5 nM) and much lower affinity for VIP (Kd>500 nM) and type II binding sites, which are widely distributed in various peripheral organs, characterised by similar affinities for PACAP and VIP (Kd=1 nM). Molecular cloning of PACAP receptors has demonstrated the existence of three distinct receptor subtypes that are abundantly spread in many tissues: the PACAP-specific PACAP receptor, coupled to different signal transduction systems, and two PACAP: VIP-indifferent receptors (VPAC1 and VPAC2, also referred to as VIPR1 and VIPR2, respectively), which are primarily coupled to adenylyl cyclase.

The exact biological and pharmacological function of PACAP is presently being investigated in many organs and tissues as in endocrine glands, central nervous system, respiratory system, cardiovascular system and gastrointestinal tract. Although extensive studies have also been performed on its function in the immune system, limited data are available concerning its function on haemostasis. An effect of PACAP on aggregation and metabolism of isolated platelets has been described [Kis et al. (1999) *Prostaglandins Other Lipid Mediat.* 58:103-112 and Ichiki et al. (1992) *Biochem Biophys Res Commun.* 187, 1587-1593]. The occurrence of the VPAC1 receptor on platelets which binds both VIP as PACAP has been reported (Park et al. (1996) *Blood* 87, 4629-4635).

SUMMARY OF THE INVENTION

The invention relates to the use of an inhibitor of PACAP signalling for the manufacture of a medicament for the prevention or treatment of thrombocytopenia. Herein the inhibitor of PACAP signalling can target expressed PACAP, expressed VIP or a receptor for PACAP. A receptor for PACAP can be the PACAP receptor (PACAPR), VPAC1 or VPAC2. The inhibitor can be an antagonist which interferes with PACAP, VIP or a PACAP receptor protein. Alternatively the inhibitor can inhibit the transcription or translation of PACAP, VIP or a receptor for PACAP. Examples of inhibitors of transcription and translation include an antisense molecule, an RNAi, an aptamer, a small molecule, an antibody, a ribozyme, a transdominant receptor, and a tetrameric peptide. Specific compounds having an inhibitory effect on PACAP signalling include max.d.4 5, PACAP6-38, [4Cl-D-Phe6, Leu17]VIP, VIP(10-28), cyclic lactam analogs of PACAP, [AcHis(1), D-Phe(2), Lys(15), Leu(17)]VIP(3-7)/GRF(8-27), PACAP receptor blocking Cyclic lactam PACAP analogs, N-terminal truncated or substituted VIP peptide PACAP receptor blockers, neutralising antibodies against VPAC(1), and neutralising aptamer against VPAC(1) receptor, [4Cl-D-Phe6, Leu17]VIP, VIP(10-28).

The invention also relates to a pharmaceutical composition comprising an inhibitor of PACAP signalling and an additional compound for enhancing megakaryocyte maturation such as thrombopoetin or Interleukin 11.

The invention also relates to the use of pituitary adenylyl cyclase activating peptide (PACAP), its derivatives, mimetics, antibodies or inhibitors for modulating the primary haemostasis or thrombocytopoiesis or the use of agonists or antagonists of the platelet receptor, VPAC1, to modulate the primary haemostasis or thrombocytopoiesis.

The present invention further relates to a method for prevention as a prophylactic and for the treatment of either thrombosis or bleeding based on administration of pituitary adenylyl cyclase activating peptide (PACAP) mimetics or inhibitors respectively.

The present invention shows that human platelets express the VPAC1 receptor.

The present invention also shows that PACAP has an important function in primary haemostasis: platelet number as well as platelet function are highly influenced by PACAP.

The invention provides compositions and methods useful for activating thrombocytopoiesis in mammals, including humans. The invention applies to human and veterinary applications. The inventive composition and method have been shown to be especially effective in treating platelet hypofunction.

In addition, the present invention finds utility in e.g., radiation treatment or chemotherapeutic treatment or sickness caused by radiation accidents, where prevention or treatment of thrombocytopenia, anemia and neutropenia is a significant concern. The depletion of hematopoietic precursors in the bone marrow associated with chemotherapy and irradiation results in hemorrhagic and infectious complications. Severe suppression of the hematopoietic system is a major factor in limiting chemotherapy use and dose escalation.

Compounds useful for exercising the thrombocytopoietic treatment or the manufacturing of a medicament for platelet hypofunction of present invention are thus compounds that inhibit the activity of PACAP or VIP and more specifically that antagonise the platelet receptor for PACAP.

DETAILED DESCRIPTION

4A: Left panel: the mean bleeding time (sec)+/−SD for 10 animals in each group (unpaired T-test; p=0.0001) from either wild type (WT) versus PACAP overexpressing (PACAP-Tg) mice. 4A Right panel: the collagen-induced (5 mg/ml) platelet aggregation in hirudinized PRP from 2 WT and two PACAP-Tg mice are shown. 4B: The left panel shows the dose-dependent stimulation by PACAP(6-38) of the collagen-induced (0.2 μg/ml) aggregation of human platelets; representative tracings of five separate experiments. The effect of PACAP (6-38) on the collagen-induced platelet aggregation (2 microgramg/ml) for patient VI:1 is illustrated in the right panel. 4C: The platelet aggregation inhibition test with collagen (2 μg/ml) and different concentrations of Iloprost (ng/ml) as indicated in the absence (left panels) and presence (right panels) of PACAP(6-38) for a control (upper panels) or patient VI:1 (lower panels).

Figure 5:
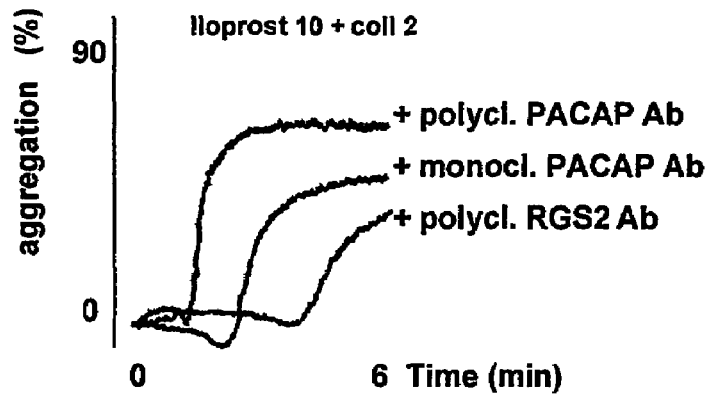
Figure 5:
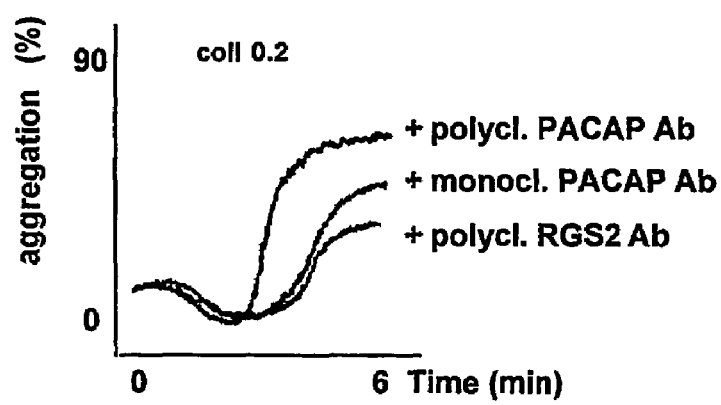
Figure 5:
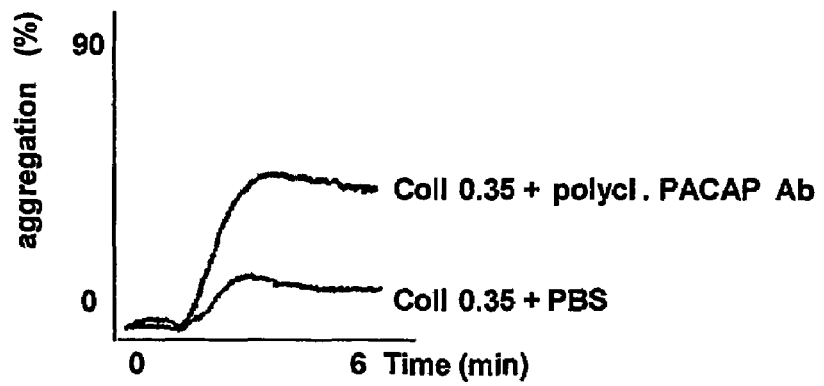
Figure 5:
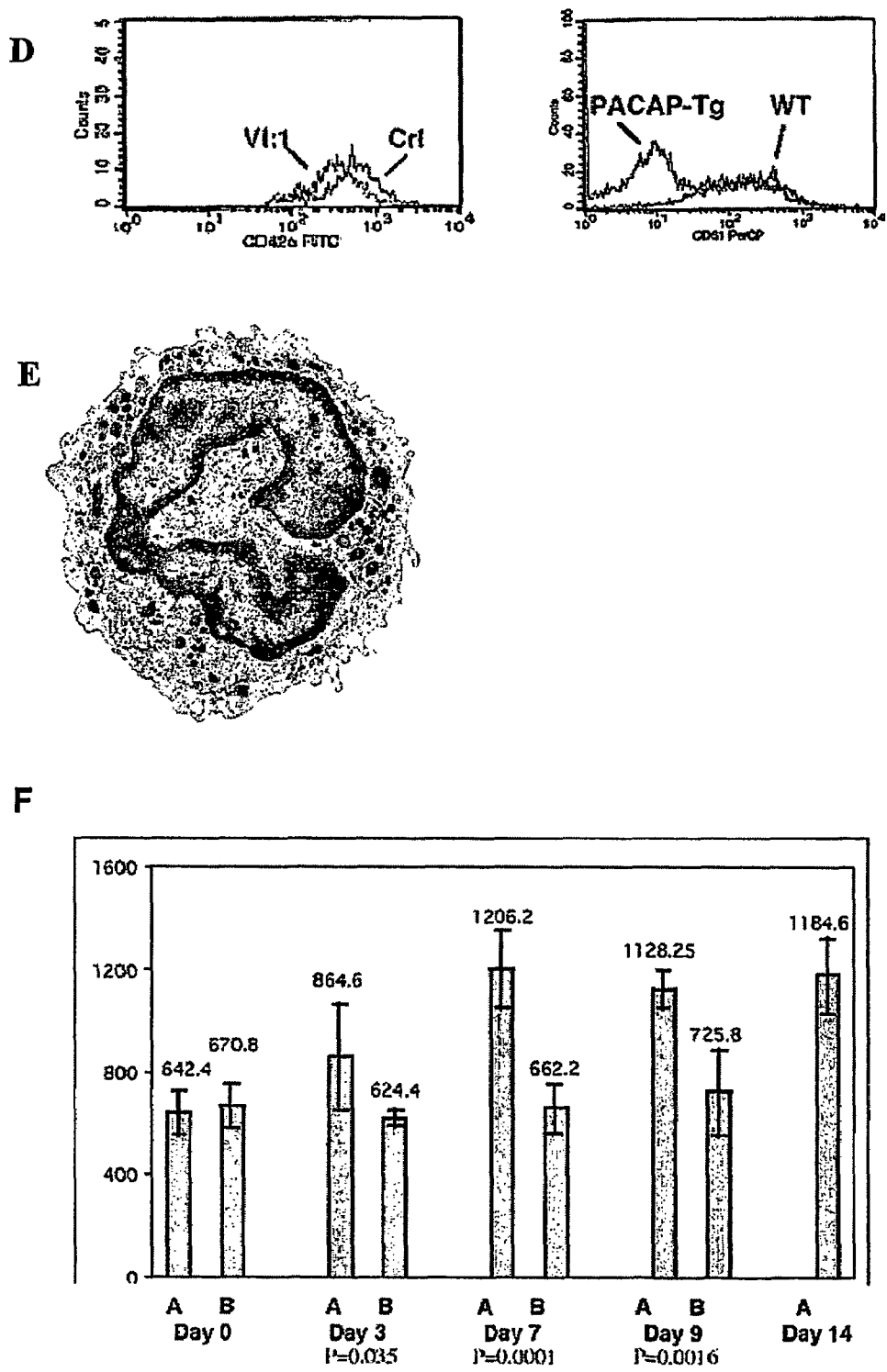

FIG. 5. Effect of anti-PACAP antibodies in mice. Platelet aggregation was performed in PRP pooled from five mice of each group with 250×10 plt/μl. 5A: The platelet aggregation inhibition test with collagen (2 μg/ml) and preincubation of Iloprost (10 μg/ml) for mice injected with the indicated antibodies. 5B: Platelet aggregation induced with a low concentration of collagen (0.2 μg/ml) for mice injected with the indicated antibodies. 5C: Stimulatory effect of a polyclonal anti-PACAP antibody (10 μg/ml) on collagen-induced (0.35 μg/ml) platelet aggregation.

Effect of PA CAP on thrombopoiesis. 5D: FACS analysis showed a reduced expression of glycoprotein IX (CD42a) in platelets from patient VI:1 versus control platelets (left panel) and a reduced expression of glycoprotein IIIA (CD61) in the megakaryocytes of the PACAP overexpressing mice compared to cells of the control mice (right panel). These experiments were repeated twice with identical results. 5E: Electron micrograph of megakaryocyte progenitor cell. Specific granules are seen as well as a dense core vesicle (arrow). A few endoplasmic reticulum cisternae are obvious. Original magnification: ×18.500. 5F: Mean platelet number+/−SD in mice (n=5) injected with either polyclonal anti-PACAP (group A) or monoclonal anti-human vWF (75H4B12) (group B) antibody, determined on the indicated days.

Figure 6:
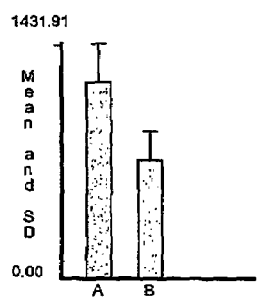

FIG. 6. The mean platelet number per μl for mice (n=5) injected with either polyclonal anti-PACAP (6A) or an irrelevant anti-β2-glycoprotein I (6B) antibody was determined 14 days after the first antibody injection.

Figure 7:
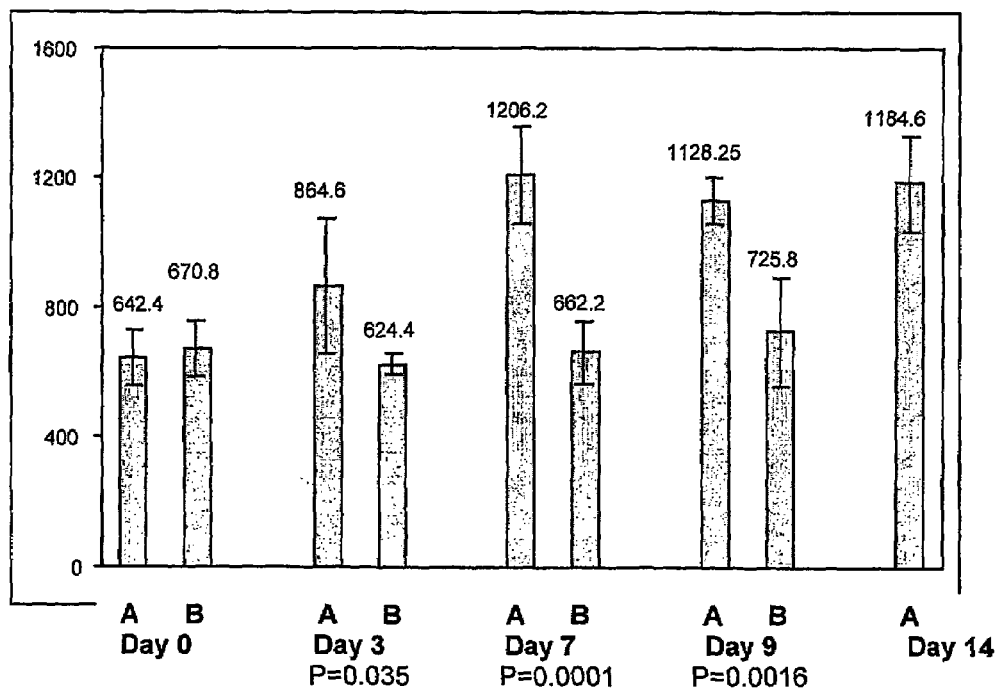

FIG. 7. Mean platelet number+/−SD for mice (n=5) injected with either polyclonal anti-PACAP (bars indicated with A) or anti-vWF (75H4B12) (bars indicated with B) antibody determined at the indicated days.

Figure 8:
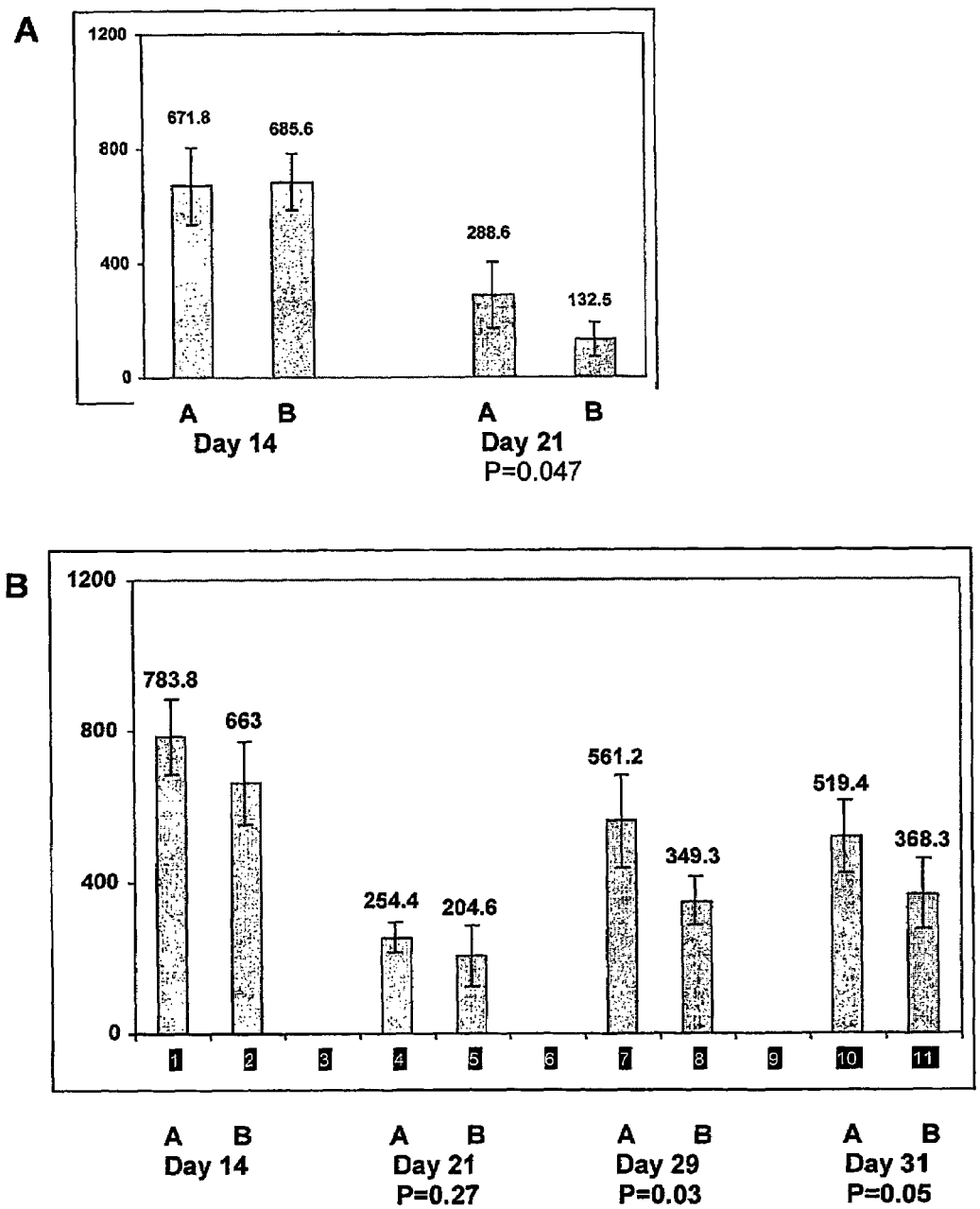

FIG. 8. Mean platelet number/μ+/−SD for mice (n=5) injected with either polyclonal anti-PACAP (bars indicated with A) or an irrelevant anti-XLαxs (bars indicated with B) polyclonal antibody determined at the indicated days. Data represent separated experiments A (top figure) and B (bottom figure).

DEFINITIONS

"PACAP" refers to Pituitary Adenylate Cyclase-Activating Polypeptide and refers to the mature and processed versions of the mature PACAP as PACAP(1-48) and more particularly to processed isoforms PACAP(1-38) HSDGIFTDSYS-RYRKQMAVKIYLAAVLGKRYKQRVKNK-NH2 [SEQ ID NO:1] and PACAP(1-27) HSDGIFTDSYSRYRKQ-MAVKKYLMVL-NH2 [SEQ ID VIP:2]. PACAP refers to PACAP of vertebrates, including mammalian PACAP and human PACAP.

"VIP" refers to Vasoactive Intestinal Peptide (VIP), a 28-amino acid peptide which exhibits a wide variety of biologic actions. Because VIP shows similarities to glucagon, secretin and gastric inhibitory peptide (GIP), it has been considered a member of the glucagon-secretin family. The primary translation product of the mRNA encoding VIP (prepro-VIP) has a molecular weight of 20 daltons.

"receptor for PACAP" refers to a receptor which is bound and activated by PACAP including the PACAP receptor (PACAPR) [OMIM 102981] which is specific for PACAP but also to VPAC1 (VIPR1) [OMIM 192321] and VPAC2 (VIPR2) [OMIM 601970] receptors which bind both PACAP and VIP (Vasoactive Intestinal peptide).

As used herein, "thrombocytopenia" is any disorder in which the platelet level in the affected individual fall below a normal range of platelet numbers for that individual, due to disturbance in production distribution or destruction. In humans, normal blood platelet levels range from about 150.000 to 300.000 per microliter peripheral blood. With a platelet level of 100.000 per microliter patients have no abnormal bleeding even with major surgery; with a platelet count of 50.000 to 100.000 per microliter, patients may bleed longer than normal with severe trauma; with a platelet count of 20.000 to 50.000 per microliter, bleeding occurs with minor trauma but spontaneous bleeding is unusual; with a platelet count of less than 20.000, patients may have spontaneous bleeding and when the platelet count is less than 10.000 per microliter, patients are at high risk for severe bleeding.

Thrombocytopenia also refers to a decrease in platelet number in an individual when compared to the platelet number measured at a certain reference point in that individual. The decrease in platelet number in the individual can be a decrease in more than 20%, 30%, 40%, 60%, 80%, 90%, 95% or even more, compared to value at the reference point. A decrease in platelet number when compared to the platelet number measured at a certain reference point, can in certain individuals be accompanied with changes in bleeding, while in other individuals a comparable decrease will not be accompanied with changes in bleeding. The reference point mentioned, can be for instance the start of a therapy such as a radiation or chemotherapy.

Thrombocytopenia includes infection-induced thrombocytopenia, treatment-induced thrombocytopenia and others.

"Infection-induced thrombocytopenia" is a disorder characterised by a lowered level of platelets in peripheral blood, which is caused by an infectious agent such as a bacteria or virus.

"Treatment-induced thrombocytopenia" is a disorder characterised by a lowered level of platelets in peripheral blood which is caused by therapeutic treatments such as gamma irradiation, therapeutic exposure to radiation, cytotoxic drugs, chemicals containing benzene or anthracene and even some commonly used drugs such as chloramphenicol, thiouracil, and barbiturate hypnotics.

"Other types of thrombocytopenia" comprise disorders characterised by a low level of platelets in peripheral blood, which are caused by any mechanism other than: infectious agents or therapeutic treatments causing thrombocytopenia. Factors causing this type of thrombocytopenia include, but are not limited to, rare bone marrow disorders such as: congenital amegakaryocytic hypoplasia and thrombocytopenia with absent radii (TAR syndrome), an increase in spleen size, or splenomegaly, caused by portal hypertension, secondary to liver disease, or macrophage storage disorders such as Gauchers disease, autoimmune disorders such as idiopathic or immune thrombocytopenic purpura (ITP), vasculitis, hemolytic uremic syndrome, thrombotic thrombocytopenic purpura (TTP), disseminated intravascular coagulation (DIC) and prosthetic cardiac valves. ITP is by far the most frequent type in this group of thrombocytopenias.

A "subject having thrombocytopenia" is a subject having any type of thrombocytopenia and includes but is not limited to non-chemotherapeutic-induced thrombocytopenia, or chemotherapeutic-induced thrombocytopenia.

"A subject at risk of developing thrombocytopenia" is a subject who has a high probability of acquiring or developing thrombocytopenia. For example, a patient with a malignant tumour who is prescribed a chemotherapeutic treatment is at risk of developing treatment-induced thrombocytopenia and a subject who has an increased risk of exposure to infectious agents is at risk of developing infection-induced thrombocytopenia.

"PACAP signalling" refers to the binding and activation of a receptor for PACAP. It thus relates to the binding of PACAP to the PACAC receptor, VPAC1 or VPAC2 r and subsequent activation. Moreover PACAP signalling also includes binding and activation of VPAC1 and VPAC2 by VIP. In a particular embodiment "PACAP signalling" relates to signalling via the VPAC1 receptor present on megakaryocytes in bone marrow.

"Inhibition of PACAP signalling" refers to the inhibition of the binding of PACAP or VIP to a receptor for PACAP, which includes inhibition of the production and/or activity of the ligands PACAP and/or VIP (PACAP or VIP inhibition by PACAP and/or VIP inhibitors) and inhibition of the production or function of one or more receptors for PACAP or the binding of PACAP or VIP thereto (PACAP receptor inhibition), e.g. by antibodies, antagonists, soluble receptors, antisense etc, as detailed herein. These molecules are also generally referred to herein as 'inhibitors of PACAP signalling'.

The term anti-PACAP antibody or antibodies' relates to an antibody or antibodies characterised as being specifically directed against PACAP, VIP or any functional derivative thereof, with said antibodies being preferably monoclonal antibodies or an antigen-binding fragment thereof, of the F(ab')2, F(ab) or single chain Fv type, or any type of recombinant antibody or antibody fragment derived thereof. Preferably, said antibody or fragment thereof is humanized or is in other ways appropriate for injection into the subject to be treated therewith.

The term 'anti-PACAP Receptor antibody or antibodies' relates to an antibody or antibodies characterised as being specifically directed against one or more of the receptors for PACAP (PACAPR, VPAC1 and VPAC2) with said antibodies being preferably monoclonal antibodies; or an antigen-binding fragment thereof, of the F(ab')2, F(ab) or single chain Fv type, or any type of recombinant antibody derived thereof.

These antibodies of the invention, including specific polyclonal antisera prepared against a receptor for PACAP, the ligands PACAP, VIP, or any functional derivative thereof, have no cross-reactivity to other proteins. The monoclonal antibodies of the invention can, for instance, be produced by any hybridoma produced according to classical methods using splenic cells of an animal, particularly of a mouse or rat immunized against a receptor for PACAP, PACAP, VIP, a molecule involved in PACAP signalling, or any functional derivative thereof, and cells of a myeloma cell line, and can be selected by the ability of the hybridoma to produce the monoclonal antibodies recognizing a receptor for PACAP, PACAP, VIP, the molecule involved in PACAP signalling, or any functional derivative thereof which has been initially used for the immunization of the animals.

The monoclonal anti-PACAP or antibodies against a receptor for PACAP according to the invention may be humanized versions of the non-human monoclonal antibodies, made by means of recombinant DNA technology, departing from the mouse and/or human genomic DNA sequences coding for H and L chains or from cDNA clones coding for H and L chains. Alternatively the monoclonal antibodies according to this embodiment of the invention may be human monoclonal antibodies. Such human monoclonal antibodies are prepared, for instance, by means of human peripheral blood lymphocytes (PBL) repopulation of severe combined immune deficiency (SCID) mice as described in: PCT/EP99/03605 or by using transgenic non-human animals capable of producing human antibodies as described in U.S. Pat. No. 5,545,806. Also fragments derived from these monoclonal antibodies such as Fab, F(ab)'2 and ssFv ("single chain variable fragment"), provided they have retained the original binding properties, form part of the present invention. Such fragments are commonly generated by, for instance, enzymatic digestion of the antibodies with papain, pepsin, or other proteases. It is well known to the person skilled in the art that monoclonal antibodies, or fragments thereof, can be modified for various uses. An appropriate label of the enzymatic, fluorescent, or radioactive type can label the antibodies involved in the invention.

"stimulation of PACAP signalling" refers to the stimulation of a signal caused by the binding of PACAP, VIP or an agonist thereof to a receptor for PACAP which includes stimulation of the production or increase of the presence of the ligands PACAP and/or VIP, or agonists thereof or stimulation of the production or activity of one or more of a receptor for PACAP or the binding of PACAP or VIP thereto (PACAP receptor stimulation), e.g. by agonists, co-expression of PACAP or VIP-like molecules, etc, as detailed herein. These molecules are also generally referred to herein as stimulators of PACAP signalling.

The term "pharmaceutically acceptable" is used to indicate that a compound used in the manufacture of the medicament is appropriate, for example with respect to specific activity or purity. The term "treatment" or "prevention" refers to any process, action, application, therapy, or the like, wherein a subject or individual is subjected to medical aid with the object of improving or maintaining the mammal's condition, directly or indirectly. Subject, individual or patient refers to a mammal and includes a laboratory animal, pet, agriculture animal; examples include dogs, cats, horses, rodents (rats, mice, hamsters, guinea pigs), cattle, pigs, rabbits, goats, among others. A mammal also refers to monkeys and primates, including humans.

The present invention relates to the modulation of platelet function and number through the inhibition of PACAP signalling.

In one aspect, the present invention relates to the inhibition of PACAP signalling by targeting PACAP and/or VIP in a subject and to compounds useful therefore. In a particular embodiment it relates to PACAP and/or VIP inhibition in the peripheral blood of a subject.

Compounds which target expressed PACAP and/or VIP (referred to herein as examples of PACAP and/or VIP inhibitors) include polyclonal or monoclonal antibodies or antibody fragments against PACAP or VIP. Other compounds targeting expressed PACAP and/or VIP include soluble fragments of PACAP receptors. Thus more specifically the invention also relates to molecules that neutralize the activity of PACAP and/or VIP by interfering with its dimerisation, receptor-binding and/or receptor-binding-mediated signal transduction. By molecules it is meant peptides, tetrameric peptides, proteins, organic molecules, mutants of PACAP or VIP, soluble receptors of the PACAP receptor (PACAPR), VPAC1 or VPAC2 and any fragment or homologue thereof having the same neutralizing effect as stated above.

In another aspect, the present invention relates to the inhibition of PACAP signalling by targeting one or more of a receptor for PACAP (capable of binding PACAP) and to compounds useful therefore.

For instance, certain (poly)peptides are known to be PACAP receptor (PACAPR) antagonists such as max.d.45 (Sakashita et al. Br. (2001) *J. Pharmacol*, 132: 1769-1776) and PACAP6-38 (Tohei et al. (2001) *Neuro-endocrinol*. 73, 68-74). Compounds with type II PACAP receptor (VPAC1 and VPAC2) antagonist properties comprise several N-terminal truncated or substituted VIP peptides such as [4Cl-D-Phe6, Leu17]VIP, VIP(10-28) (Pandol et al. (1986) *Am. J. Physiol*. 250: G553-G557; Turner et al. (1986), *Peptides* 7: 849-854; Gozes et al. (1995) *Cell Mol Neurobiol*. 15, 675-687; Gourlet et al. (1997) *Peptides* 18, 155-560), cyclic lactam analogs of PACAP (Bitar et al. (1994) *Peptides* 15: 461-466). VPAC1 receptor selective antagonists known are for instance [AcHis(1), D-Phe(2), Lys(15), Leu(17)]VIP(3-7)/GRF(8-27) (Lema-Kisoka R et al. (2001) cited supra). Other PACAP receptor agonists are neutralising antibodies against VPAC1 or aptamers (3-dimensional nucleic acids that bind to molecular targets in a manner similar to antibodies) that bind to VPAC1 receptor (or against PACAP) thereby neutralising its activity. Antagonising peptides MAX65 and MAX65 NH$_2$ are described in U.S. Pat. No. 6,017,533. VIP antagonising peptides with modified amino and carboxyterminal groups are described in WO95/21294. Other VIP antagonising compounds are described in U.S. Pat. No. 5,217,953, U.S. Pat. No. 5,565,242, and U.S. Pat. No. 6,630,124.

Small molecules that act as a PACAP receptor antagonist, e.g. small organic molecules and other drug candidates can be obtained, for example, from combinatorial and natural product libraries. Random peptide libraries, such as the use of tetrameric peptide libraries such as described in WO0185796, consisting of all possible combinations of amino acids attached to a solid phase support may be used in identifying compounds useful in the present invention. Also transdominant-negative mutant forms of PACAP-receptors (e.g. a transdominant-negative receptor of VPAC1 or VPAC2 can be used to inhibit the signal transduction of PACAP or VIP.

Thus, one aspect of inhibition of PACAP signalling refers to inhibition at the protein level (PACAP or VIP or any of a receptor for PACAP). The inhibition of PACAP signalling leads to a diminished interaction with its receptor and an inhibition of signal transduction. Preferably said inhibition is at least 20%, 30%, 40%, 50%, 60%, 70%, 80%, 90% or even higher. The inhibition of compounds on PACAP signalling can be measured for example by platelet aggregation or measuring the release of compounds from platelets such as ATP or serotonin. The biological activity of other potential PACAP agonists or antagonist can be determined by (1) determining whether the compound binds to receptors for PACAP (Gottschall, et al. (1990) *Endocrinology* 127, 272; EP Application 529 487) and (2) determining whether the compound stimulates the production or release of PACAP. This can be assayed on isolated platelets or megakaryocytes or can be assayed in a cell culture system wherein cells are transfected with PACAPR, VPAC1 or VPAC2.

In another aspect, the present invention relates to the inhibition of PACAP signalling by preventing expression (transcription and/or translation) of the PACAP and/or VIP gene and/or by preventing expression of a receptor for PACAP in blood platelet precursors and to compounds useful therefore. This inhibition is particularly effective when done in hematopoietic stem cells or in megakaryocytes or precursor cells thereof.

Examples of molecules that are useful for this aspect of the invention are anti-sense RNA and DNA molecules (e.g. polynucleotide sequences) or ribozymes that function to inhibit the translation.

Small molecules can also interfere by binding on the promoter region of a gene and inhibiting the binding of a transcription factor on said promoter region so that no mRNA is produced.

Also within the scope of the invention is the use of oligoribonucleotide sequences that include anti-sense RNA and DNA molecules and ribozymes that function to inhibit the translation of VPAC1 or VPAC2 mRNA or PACAP mRNA or VIP mRNA. Anti-sense RNA and DNA molecules act to directly block the translation of mRNA by binding to targeted mRNA and preventing protein translation. With regard to antisense DNA, oligodeoxyribonucleotides derived from the translation initiation site can be used. Ribozymes are enzymatic RNA molecules capable of catalysing the specific cleavage of RNA. The mechanism of ribozyme action involves sequence specific hybridisation of the ribozyme molecule to complementary target RNA, followed by an endonucleolytic cleavage. Within the scope of the invention are engineered hammerhead motif ribozyme molecules that specifically and efficiently catalyse endonucleolytic cleavage of VPAC(1) RNA, PACAP RNA or VIP RNA sequences. Specific ribozyme cleavage sites within any potential RNA target are initially identified by scanning the target molecule for ribozyme cleavage sites, which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors, which incorporate suitable RNA polymerase promoters such as the T7 or SP6 polymerase promoters. Alternatively, antisense cDNA constructs that synthesize anti-sense RNA constitutively or inducible, depending on the promoter used, can be introduced stably into cell lines.

Inhibition of PACAP signalling through gene transcription and/or translation by these compounds according to the present invention is at least 20%, 30%, 40%, 56%, 60%, 70%, 80%, 90% or even higher and can be measured by lowered mRNA or protein levels.

The invention in one aspect relates to a method for increasing or maintaining platelet counts in a subject having thrombocytopenia or a subject at risk of developing thrombocytopenia, by administering to the subject an inhibitor of PACAP signalling.

Thus the invention relates to the use of an inhibitor of PACAP signalling for the manufacture of a medicament for the prevention or treatment of thrombocytopenia.

The prevention or treatment against thrombocytopenia can be aimed at an increased level of active platelets. This means that platelet number becomes higher after administration of the inhibitor than prior to the administration. An amount effective to increase platelet counts in the subject is an amount, which causes an increase in the amount of circulating platelet levels. The actual levels of platelets achieved will vary depending on many variables such as the initial status of the immune system in the subject, i.e., whether the subject has mild to severe thrombocytopenia (e.g., resulting from an autoimmune disease or splenic sequestration). In general, the platelet levels of a subject who has severe thrombocytopenia will initially be very low. Any increase in the platelet levels of such a subject, even an increase to a level that is still below a normal level, can be advantageous to the subject, since at the same time platelet function will be upregulated. The administration of the inhibitor aims to increase the number of platelets by at least 20, 50, 75 or 100%. Depending on the initial status of the individual (severe or low thrombocytopenia or normal platelet number), the individual will, after the administration of the inhibitor, display a low thrombocytopenia, a normal platelet number or a platelet number of normal levels). Alternatively, and more particularly in case of prevention of thrombocytopenia e.g. in combination with or before chemotherapy, administration of an inhibitor of the PACAP signalling pathway can be aimed at a maintenance of the number of active platelets (i.e. preventing a significant decrease in the number of platelets expected as a result of chemotherapy).

The compositions for inducing platelet production, comprising an effective quantity of a PACAP inhibitor and/or VIP inhibitor and/or a PACAP receptor inhibitor can be in admixture with pharmaceutically acceptable diluents, carriers or excipients. This property of stimulating platelet production of the molecule should render it a useful adjunct in the therapy of patients suffering from acute thrombocytopenia, for example, as a result of chemo- or radiotherapy of various cancers. Currently, such patients are at grave risk when circulating platelet levels are depressed to levels whereby thrombogenesis is precluded.

In a particular embodiment the present invention relates to a pharmaceutical composition comprising an inhibitor of PACAP signalling and an additional compound for enhancing megakaryocyte maturation such as thrombopoetin or Interleukin 11.

The term medicament relates to a composition comprising molecules as described above and a pharmaceutically acceptable carrier or excipient (both terms can be used interchangeably) to treat diseases as indicated above. Suitable carriers or excipients known to the skilled man are saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier, that does not itself induce the production of antibodies harmful to the individual receiving the composition such as proteins, polysaccharides, polylactic acids, polyglycolic acids, polymeric amino acids and amino acid copolymers. The 'medicament' may be administered by any suitable method within the knowledge of the skilled person. The preferred route of administration is parenterally. For parenteral administration, the medicament of this invention will be formulated in a unit dosage injectable form such as a solution, suspension or emulsion, in association with the pharmaceutically acceptable excipients as defined above. However, the dosage and mode of administration will depend on the individual. Generally, the medicament is administered so that the compound, protein, polypeptide, peptide of the present invention is given at a dose between 1 µg/kg and 10 mg/kg, more preferably between 10 µg/kg and 5 mg/kg, most preferably between 0.1 and 2 mg/kg. Preferably, it is given as a bolus dose. Continuous infusion may also be used and includes continuous subcutaneous delivery via an osmotic minipump. If so, the medicament may be infused at a dose between 5 and 20 µg/kg/minute, more preferably between 7 and 15 µg/kg/minute.

Another aspect of administration for treatment is the use of gene therapy to deliver the above mentioned anti-sense gene or functional parts of the VPAC(1) gene, PACAP gene or VIP gene or a ribozyme directed against the VPAC(1) mRNA, PACAP mRNA, VIP mRNA or a functional part thereof or a genetic construct encoding a transdominant-negative mutant form of VPAC(1)-receptors. Gene therapy means the treatment by the delivery of therapeutic nucleic acids to patient's cells (extensively reviewed in Lever and Goodfellow (1995) *Br. Med. Bull.* 51, 1-242; Culver et al. (1995) *Br. Med. Bull.* 51, 192-204; Ledley, F. D. (1995) *Hum. Gene Ther.* 6, 1129). Gene therapy requires a method for delivering genes to the patient's cells and additional methods to ensure the effective production of any therapeutic genes. There are two general approaches to achieve gene delivery; these are non-viral delivery and virus-mediated gene delivery.

Another aspect of the invention relates the use of an inhibitor of PACAP signalling, i.e. a compound that inhibits the expression and/or activity of PACAP or, VIP gene or a PACAP or VIP protein, for the manufacture of a medicament for treatment of platelet hypofunction. This is based on the finding that platelet hypofunction can be treated (activated) by inhibiting the expression and/or activity of PACAP.

An embodiment of the present invention relates to the use of molecules which comprise a region that can specifically bind to PACAP or to one of its receptors such as (VPAC(1) receptor) and which consequently interfere with the binding of PACAP and/or VIP to the VPAC(1) receptor, interfering with the signal transduction of PACAP and/or VIP. Said molecules can be used for the manufacture of a medicament for treatment of platelet hypofunction.

Yet another aspect of the present invention relates to the use of stimulators of PACAP signalling in the prevention and treatment of thrombolytic disorders. Examples of stimulators of PACAP signalling include the 38-amino acid form of PACAP (PACAP38), HSDGIFTDSYSRYRKQMAVKKY-LAAVLGKRYKQRVKNK-NH2 (SEQ ID NO:1) and PACAP27, a 27-residue alpha-amidated polypeptide, HSDG-IFTDSYSRYRKQMAVKKYLAAVL-NH2 (SEQ ID NO:2), which are both potent agonists of PACAP/VIP receptors. Based on their binding affinity and adenylyl cyclase stimulating properties, PACAP 2-38, PACAP 2-27, AcHIS1 PACAP1-27, Ala2 PACAP (1-27) have also been demonstrated to be potent agonists of PACAP/VIP receptors (Vaudry D. et al. cited supra).

Amino acid substitutions and additions of a fatty acyl moiety have led to the development of lipophilic VIP derivatives that exhibit enhanced potency and specificity for VPAC receptors (Gozes and Fridkin, (1992) *J. Clin. Invest* 90: 810-814; Gozes et al. (1995) *Cell Mol. Neurobiol.* 15: 675687; Gourlet et al. (1998) *Eur. J. Pharmacol* 354: 105-111).

PACAP receptor (PACAPR) selective agonists are, for instance, the compounds of the group consisting of the PACAP, VIP, [K(15),R(16),L(27)]VIP(1-7)/GRF(8-27), [R(16)]ChSn), (Lundberg et al. (2001) *Endocrinology* 142, 339-347; Lema-Kilsoka R et al. (2001) *Peptides* 22, 2155-2162), [(11,22,28)Ala]-VIP (Anderson C. M. et al. (2003) *Br. J. Pharmacol.* 138, 564-73).

Agonists of the type II PACAP receptor, VPAC1 are for instance compounds of the group consisting of [R(16)]-PACAP(1-23) and [(L22)]-VIP (Van Rampelbergh et al. (2000) *Br. J. Pharmacol.* 130: 819-26) and (Lys15, Arg 6, Leu27)VIP1-7 GRF8-27 (Moody T W et al., (2000) *Ann-N.Y. Acad. Sci.* 921, 26-32).

An important embodiment of this aspect of the present invention relates to compositions comprising an activator of PACAP and/or a PACAP receptor agonist, preferably a VPAC (1) receptor agonist for treatment (particularly the prevention or suppression) of platelet hyperfunction in a subject. It can be a pharmaceutical composition, which comprises an amount of PACAP or a mimetic thereof effective for blocking or preventing thrombosis in a subject, and a pharmaceutically effective carrier. This pharmaceutical composition can be used to treat a subject having a thrombus or at risk of thrombus formation or to manufacture a medicament to treat a subject having a thrombus or at risk of thrombus formation.

The present invention demonstrates that a pharmaceutical composition, which comprises an effective amount of above mentioned PACAP/VIP receptor agonist and a pharmaceutically effective carrier can be used to decrease platelet hyperfunction and/or for blocking or preventing thrombosis formation in a subject. Such pharmaceutical composition can be used to manufacture a medicament to treat a subject having a thrombus or at risk of thrombus formation.

The invention thus provides compositions and methods useful for inhibiting, suppressing or ameliorating platelet hyperfunction in mammals, including humans. The invention has both human and veterinary applications. The inventive composition and method have been shown to be especially effective ink preventing thrombosis formation. A new class of pharmaceutical compositions and methods of treatment and prevention of thrombosis and thrombosis related injury and disease is provided.

The present invention also provides a pharmaceutical composition, which comprises an activator of PACAP or a PACAP receptor agonist, which in combination with an other antithrombotic agent, in an amount and proportion for enhancing the action of the other antithrombotic agent (e.g. aspirin, or an agent which blocks glycoprotein IIbIIIa, heparin, warfarin, coumarin derivatives, thrombin inhibitors, or Factor Xa inhibitors) to prevent clotting or dissolve clots which have already formed.

The present invention also provides a pharmaceutical composition, which comprises an activator of PACAP or a PACAP receptor agonist, in combination with an other antithrombotic agent, in an amount and proportion for enhancing the action of thrombolytic (e.g. staphylokinase, streptokinase, urokinase, tissue plasminogen activator, plasmin, mini- or microplasmin) to dissolve clots which have already formed In addition, the present invention finds utility in other contexts where prevention of platelet hyperactivity is a significant concern, e.g. acute coronary syndrome, myocardial infarction, acute myocardial infarction, unstable angina, refractory angina, peripheral vascular disease, occlusive coronary thrombus occurring post-thrombolytic therapy or post-coronary angioplasty, a thrombotically mediated cerebrovascular, syndrome, embolic stroke, thrombotic stroke, transient ischemic attacks, venous thrombosis, deep venous thrombosis, pulmonary embolus, coagulopathy, disseminated intravascular coagulation, thrombosis following angioplasty, restenosis following angioplasty, thrombosis following carotid endarterectomy, thrombotic thrombocytopenic purpura, thromboangitis obliterans, thrombotic disease associated with heparin-induced thrombocytopenia, thrombotic complications associated with extracorporeal circulation, thrombotic complications associated with instrumentation such as cardiac or other intravascular catherization, intraaortic ballon pump, coronary stent, atherosclerosis, or cardiac valve, disorder is characterized by transient ischemic attacks, and conditions required the fitting of prosthetic devices.

EXAMPLES

The following examples illustrate preferred features of the invention, but are not intended to limit the invention in any way. All of the starting materials and reagents disclosed below are known to those skilled in the art, and are available commercially or can be prepared using well-known techniques.

Methodology

Platelet Aggregation.

Blood was anticoagulated with 3.8% (wt/vol) trisodium citrate (9:1) and platelet-rich plasma (PRP), obtained by centrifugation (15 minutes at 150 g), was recentrifuged (3000 g for 15 min) to obtain platelet-poor plasma (PPP-trisodium citrate). Finally the platelet count in the PRP was adjusted for $250 \times 10^9$ platelets/L with PPP. Platelet aggregation was performed on two dual-channel Chrono-Log Aggregometers (Chronolog Corp.), by simultaneously recording 4 tracings.

Aggregation inhibition studies were done as described before (Freson et al. (2002) *Thromb. Haemost.* 86:733-738; Freson et al., (2003) *Hum. Mol. Genet.* 15:1121-1130) and involved dose-response curves to the stable prostacyclin analogue and Gs agonist Iloprost (Ilomédine; 0-5 ng/ml; Schering), which was added to PRP 1 min prior to induction of aggregation by Horm collagen (Nycomed, Germany; 2 mg/ml). The 50% inhibitory concentration (IC50) was calculated after curve fitting using the software InStat 2.03. The IC50 values±SD were compared to the IC50 for the same Gs-agonist on control platelets, studied simultaneously.

Bleeding Time and Platelet Aggregation in PACAP Overexpressing Mice.

The bleeding time was determined as described before (Foster et al. (2001) *J Clin Invest.* 107:1591-1598.). Eight- to 15-week-old mice were bled under sodium pentobarbital anesthesia from the retro-orbital plexus. Mouse blood was collected in a saline solution containing 20 µg/mL hirudin. Preparation of PRP and aggregation were done as described above.

cAMP Detection in Platelets.

Platelet cAMP was measured after incubating citrated PRP with Iloprost (1 ng/ml), arresting the reaction at different time points by addition of 12% trichloroacetic acid and using a cAMP enzyme-immunoassay (Amersham, Pharmacia Biotech). Basal cAMP levels in the platelets were measured in the presence of the phosphodiesterase inhibitor 3-isobutyl 1-methylxanthine (IBMX, 100 mM f.c.).

Human Skin Fibroblasts and cAMP Detection.

Skin fibroblasts were obtained via punch biopsy from the volar side of the upper arm. Fibroblasts were cultured in DMEM/H12 (Invitrogen) supplemented with 10% fetal bovine serum and antibiotics (Invitrogen), at 37° C. in a 5% CO2 humidified incubator. Only fibroblasts of low passage number (between 6 and 12) were used for DNA and RNA extraction and for Camp measurements. Cells were grown to 100% confluence and then incubated in serum-free medium for 24 hours before cAMP analysis. Fibroblasts were plated in duplicate, one plate used for the assay, the other for cell counting; the obtained cAMP levels were thus adjusted for the cell number. Patient or control fibroblasts were stimulated with the Gs agonist isoproterenol (Calbiochem) at 1 mM in the presence of a phosphodiesterase inhibitor (IBMX; 100 mM) and reactions were terminated by the cell lysis buffer supplied with the kit. The cAMP levels were measured using the cAMP enzyme-immunoassay mentioned above.

FISH Analysis.

FISH-analysis was performed on metaphase spreads following standard procedures (Pinkel et al. (1986). *Proc. Natl. Acad. Sci. USA.* 83: 29342938.), using a biotin labelled YAC 841C3 (Chang et al. (1993). *Genomics.* 17:393-402.) probe including the PACAP gene (ADCYAP1) locus at 18p11.31-32 in combination with two centromeric probes for chromosome 18 and 20.

Semi-Quantitative Detection of PACAP(1-38) mRNA.

Total RNA was extracted from cultured fibroblasts using TRIzol reagent according to the manufacturer's protocol.

Approximately 1 mg of DNaseI-treated fibroblast RNA, in the presence of an Rnasel inhibitor, was used for oligo (dT)-primed first strand cDNA synthesis using M-MLV reverse transcriptase (RT). The reverse transcriptase reaction was terminated by heating for 5 min at 95° C. The cDNA content was normalized using primers for b-actin. The following primer sets were used to generate specific fragments: b-actin beta5F 5'-ACCAACTGGGACGACATGGAG-3' [SEQ ID NO: 6] and beta3R 5'-CGTGAGGATCTTCATGAGG-TAGTC-3' [SEQ ID NO: 7] and PACAP(1-38) PACAP4F 5'-GMGCACCTGCAGTCGCTCG-3' [SEQ ID NO: 8] and PACAP 2R 5'-TGTATACACAGGGTAGC-3' [SEQ ID NO: 9]. All PCR reactions (with 17 and 20 cycles) were also performed in duplicate on separate fibroblast RNA samples.

Detection of PACAP in Plasma by ELISA.

Blood was anticoagulated with 3.8% (wt/vol) trisodium citrate (9:1) or acid citrate dextrose (ACD), pH 6.5 (9:1) and plasma (PPP) was obtained by centrifugation for 15 minutes at 3,000 g. A polyclonal anti-PACAP antibody was coated overnight at 4° C. in microtiter plates (Costar, high binding) at 10 mg/ml in 200 ml PBS. After blocking the plates with 1% nonfat dry milk in PBS, plasma samples (0-0.01 ml/200 ml) were deposited in the wells in PBS supplemented with 1% nonfat dry milk and 0.002% (v/v) Tween 80, overnight at 4° C. Bound PACAP(1-38) was revealed with secondary horseradish peroxidase-conjugated polyclonal anti-PACAP antibody (dilution 1/2500) and 0-phenylenediamine. A dilution series of recombinant PACAP(1-38) served as a quantitative standard. All animal experiments were approved by the institutional review board and were conducted according to the guidelines for animal experiments of the National Institutes of Health.

Example 1

Generation of Megakaryocyte-Specific PACAP Overexpressing Mice

The murine GPIIb promoter (extending from +23 to 508 relative to the initiation start site) was excised from the mGPIIb-pGL3 plasmid by digestion with KpnI and BamHI and inserted into the KpnI-BamHI-digested PACAP-pcDNA3.1 vector (Invitrogen) in front of the mouse PACAP gene (Denarier et al. (1993), *Biochem. Biophys. Res. Com-* mun. 195:1360-1364). The mouse PACAP gene was amplified from brain cDNA with primers mPACAP1R 5'-GTAGC-CGCTCGAGGATCTGCTACAAGTATGC-3' [SEQ ID NO: 3] and mPACAP4F 5'-GTTAGCCGAATTCAGTTCMG-GTCTGGCTAG-3' [SEQ ID NO: 4], sequenced, and cloned into the EcoRI-XhoI site of the pcDNA3.1 vector. The 2.2-kilobase (kb) KpnIDraIII fragment (GPIIb-PACAP) was excised and purified for zygote injection. The GPIIb promoter has been successfully used to restrict transgene expression to the megakaryocytic cell lineage of mice (Tronick-Le Roux et al. (1995) *J. Exp. Med.* 181:2141-2151). Transgenic PACAP overexpressing mice were generated by zygote injection into the Friend leukemia virus, strain B (FVB) background according to previously published plocedures (Oury et al. (2003) *Blood.* 101:3969-3976; Holvbet et al. (1997) *Eur. J. Biochem.* 245:642-647). Transgenic offspring were identified by PCR screening using genomic DNA extracted from tail samples. The following primer pair was used: mGPIIb1F 5'-TGGCCACATCACAGCATTCMG-3' [SEQ ID No: 5] and mPACAP1R Example 2

PACAP Overexpression in Patients

A. Patient Descriptions

Figure 1:
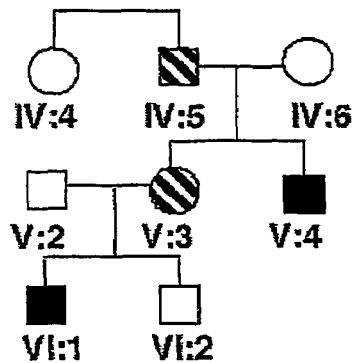
FIG. 1. Family presentation. Squares, male; circles, female; filled symbols, affected individuals; open symbols, unaffected individuals. Patient (VI:1) is the priopositus. Black filled symbols represent members with severe mental retardation and a partial trisomy 18p and monosomy 20p, striped boxes represent members with borderline IQ and the balanced translocation t(18;20) (p21;p13) while question marks stand for members with unexplained mental retardation but unknown karyotype.

FIG. 1 represents a family characterised by an unbalanced segregation of the reciprocal translocation t(18;20) (p21; p13), of which different members suffer from unexplained mental retardation. The propositus (VI:1) is a 23-year-old boy with a hypogonadotropic hypogonadism and is followed for epilepsy, severe mental retardation, hyperactive behaviour and hypotonia. He has an increased bleeding tendency and the Ivy bleeding time was markedly prolonged (>15 minutes) but coagulation studies are normal. Electron microscopy of his platelets is completely normal but he presented on different occasions with a moderate thrombocytopenia, as his platelet count is always about 70-90×10$^3$ platelets/µl. His karyotype shows a partial trisomy 18p and monosomy 20p. His brother (VI:2), father (V:2) and maternal grandmother (IV:6) are phenotypically normal, have no bleeding problems and have a normal karyotype. In contrast, his mother (V:3) and maternal grandfather (IV:5) have no obvious neurologic abnormalities but a borderline IQ. They carry the balanced translocation t(18,20) (p21,p13). They don't have any obvious bleeding problems and have a normal platelet count. His 47-year-old uncle (V:4) also suffers from severe mental retardation, pronounced recurrent epistaxis and cryptorchidism. Furthermore, he frequently has gastric bleedings and his platelet count is around 150×10$^3$ platelets/µl. He also has a partial trisomy 18p and monosomy 20p. Two other family members (IV:2 and V:1) are known with unexplained mental retardation but from these individuals no DNA samples or further clinical information are available.

B: Adenylyl Cyclase Activity in Platelets and Fibroblasts

The propositus VI:1 has disturbed platelet function with a gain-of-Gs activity measured by the platelet aggregation inhibition test, similar to patients with the XLαs insertion (Vaudry et al. (2000) cited supra; Freson et al. (2001) Thrombosis and Haemostasis 86:733-738). Platelets from the patients (VI:1 and V:4) with the partial trisomy 18p/monosomy 20p had a significantly increased sensitivity towards a Gs agonist, the prostacyclin analogue Iloprost (table 1), while platelets from the family members (IV:5 and V:3) with the balanced translocation showed a moderately increased sensitivity. The IC$_{50}$ value for member IV:6 with the normal karyotype is within the rage of the IC$_{50}$ values from 22 unrelated controls.

An important difference between patients from this family and the patients with the XLαs insertion is their decreased sensitivity towards the platelet agonist such as collagen, ADP and U46619. The collagen concentration to obtain 50% aggregation for platelets from V:4 and VI:1 is significantly higher than for platelets from unrelated controls or the normal member IV:6 (Table 1). The reactivity of platelets from IV:5 and V:3 towards collagen is again mildly affected.

TABLE 1

IC$_{50}$ value for Iloprost in the platelet aggregation inhibition test

|  | IC$_{50}$ ± SD Iloprost | EC$_{50}$ ± SD Collagen |
|---|---|---|
| IV:6 | 0.96 ± 0.002 | 0.25 ± 0.012 |
| IV:5 | 0.50 ± 0.003* | 0.74 ± 0.013 |
| V3 | 0.47 ± 0.003* | 0.75 ± 0.006 |
| V4 | 0.27 ± 0.005** | 1.08 ± 0.006 |
| VI:1 | 0.34 ± 0.004** | 1.03 ± 0.008 |
| controls | 1.04 ± 0.39 (n = 22) | 0.22 ± 0.6 (n = 10) |

IC$_{50}$ ± accuracy values for indicated individuals and the mean IC$_{50}$ value for Iloprost in the platelet aggregation inhibition test with 2 µg/ml collagen in 22 controls were calculated. A significantly (P ≦ 0.03* or P ≦ 0.0076**) lower IC$_{50}$ value indicates a Gs hyperfunction.The right column of this table illustrates the significantly decreased response to collagen (µg/ml) for respectively IV:5 and V:3 (P ≦ 0.003*) versus V:4 and VI:1 (P ≦ 0.0001**) compared to 10 controls or IV:6. EC$_{50}$ is expressed as collagen concentration that induces aggregation with amplitude 50% of maximal aggregation.

For patients with the XLαs insertion, it has been shown that the functional responses mediated by stimulation of Gs agonists are due to hyperactivity of adenylyl cyclase only when Gs-coupled receptors are stimulated (Vaudry et al. (2000) cited supra; Freson et al. (2001) cited supra). These patients had normal basal cAMP levels. This indicates, that in the platelets of the propositus VI:1, adenylyl cyclase is already activated under basal conditions. In addition to an in creased cAMP response to Iloprost, patient VI:1 indeed shows higher basal cAMP levels (FIG. 2A). cAMP levels were measured in fibroblasts from VI:1. A similar increased basal and stimulated cAMP response (FIG. 2B) was found.

C. PACAP(1-38) mRNA and Protein Overexpression

Figure 2:
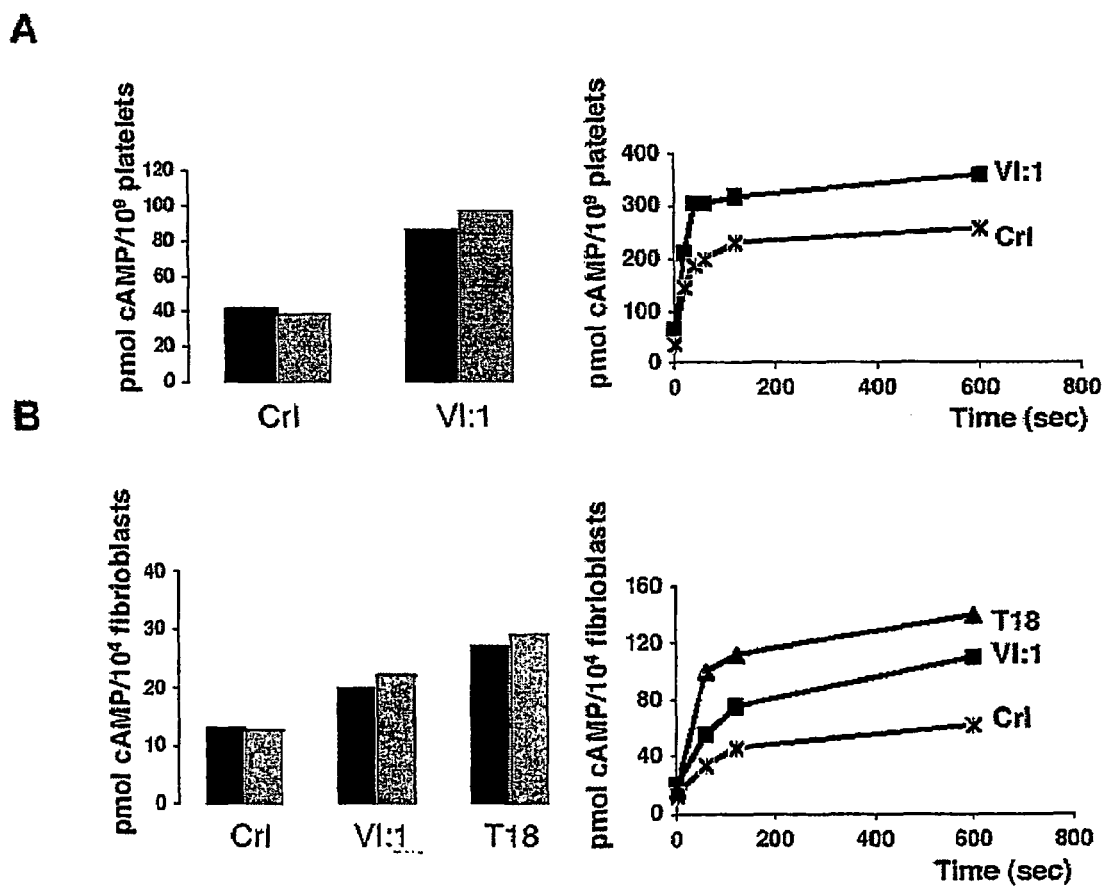
FIG. 2. Platelet aggregation and adenylyl cyclase activity. Measurements of cAMP levels under basal conditions (2A) performed in duplicate (left panel) or after stimulation with Iloprost (1 ng/ml) (2B) for various time intervals (right panel) in platelets from VI:1 (■) or an unrelated control (Crl)(X). Measurements of cAMP levels under basal conditions performed in duplicate (left panel) or after stimulation with isoproterenol (1 μM) for various time intervals (right panel) in fibroblasts from VI:1, a patient with trisomy 18 (▲) or an unrelated, control (Crl) (X). All cAMP measurements were performed in the presence of the phosphodiesterase inhibitor IBMX (400 μM).

Patient VI:1 has a normal Gsα mRNA and protein expression level and the coding sequence for the Gsα gene and XL-exon1 were completely normal. Since this patient had a partial trisomy 18p and monosomy 20p, these chromosomes were screened for candidate genes. Interestingly, measurement of the adenylyl cyclase activity in fibroblasts from an unrelated patient with a complete trisomy 18 showed similarly increased basal and stimulated cAMP levels (FIG. 2B). The gene for PACAP (ADCYAP1) is located on chromosome 18p31-32 (Hosoya M. et al. *Biochim Biophys Acta* (1992) 1129, 199-206.) and is a possible candidate since its active peptide, PACAP(1-38), stimulates Gs-coupled receptors and thereby activates adenylyl cyclase. FISH analysis with YAC clone Y841C3 (Chang E. et al. *Genomics* (1993) 17: 393-402.), that contains ACDYAP1, showed that the translocation results in three copies of the gene in patients VI:1 and V:4.

Human skin fibroblasts express PACAP(1-38) and the PACAP type1-receptor (VPAC1) (Steinhoff M, et al. *Regul Pept* (1999), 80: 49-55,). PACAP(1-38) mRNA was overexpressed in fibroblasts from patient VI:1 (FIG. 3A) by semi-quantitative RT-PCR. No PACAP mRNA was found in platelets by RT-PCR, probably due to their unstable RNA.

Figure 3:
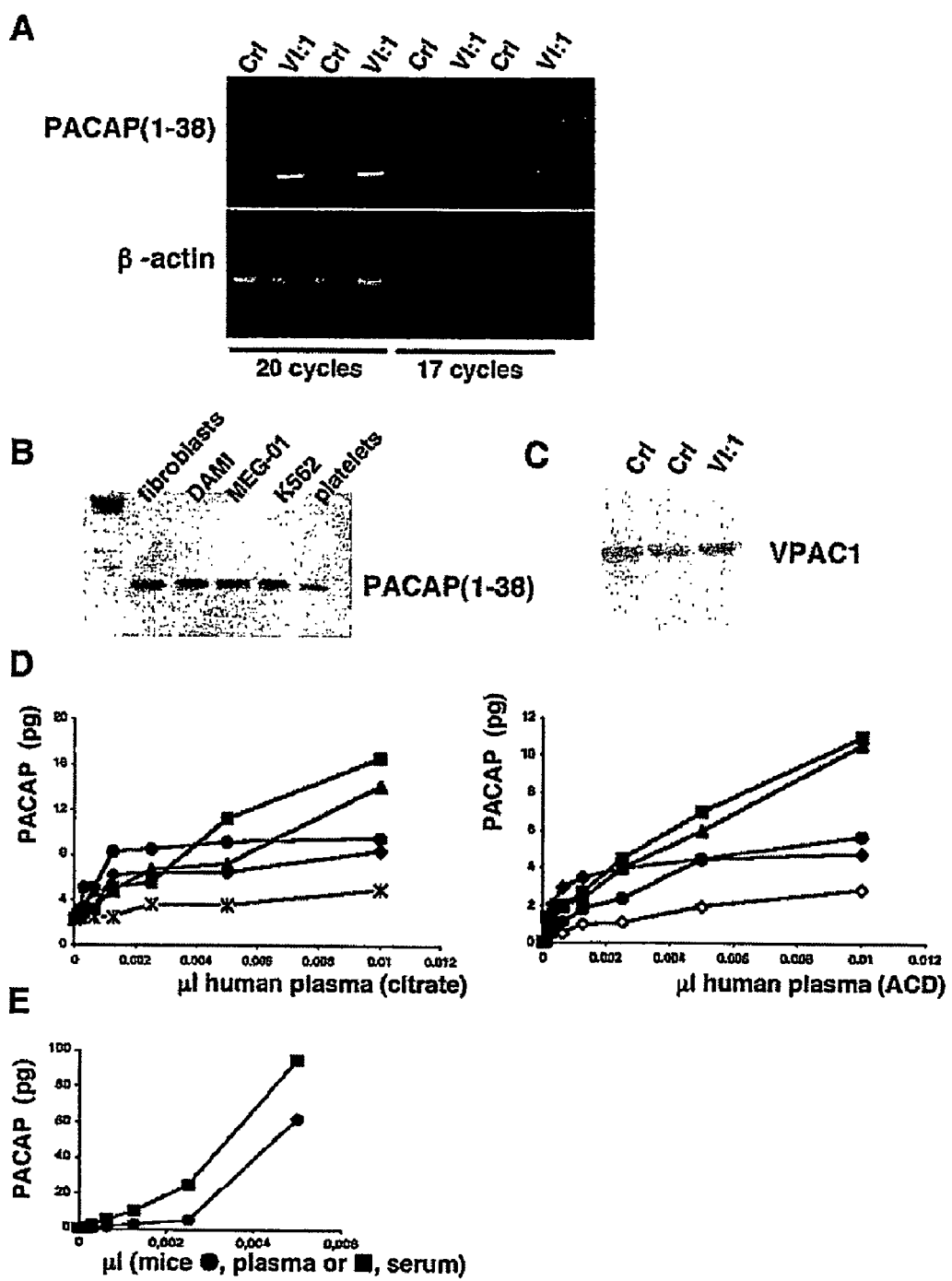
FIG. 3. PACAP detection in fibroblasts and plasma. 3A: Semi-quantitative RT-PCR using 20 cycles and 17 showed PACAP(1-38) overexpression in fibroblasts from patient VI:1 compared with two controls. β-actin is the internal control. 3B: PACAP mRNA detection in fibroblasts, megakaryocytic cell lines DAMI, MEG-01 and K562, and platelets was performed by RT-PCR. 3C: Immunoblot analysis of the VPAC1 receptor (58 kDa) in platelets from two unrelated controls and patient VI:1. 3D PACAP detections by ELISA in plasma from citrate (left panel) or ACD (acid citrate dextrose) (right panel) blood show pronounced or moderately increased PACAP level in respectively VI:1 (■) and V:4 (▲) or IV:5 (●) and V:3 (♦) versus a citrated plasma pool (*) or IV:6 (◇). 3E. PACAP levels detected by ELISA in plasma (I) or serum (n) from mice (n=3). 3F. Collagen induced aggregation of control platelets in plasma from a control or from patient IV:1 (two experiments shown).
Figure 3:
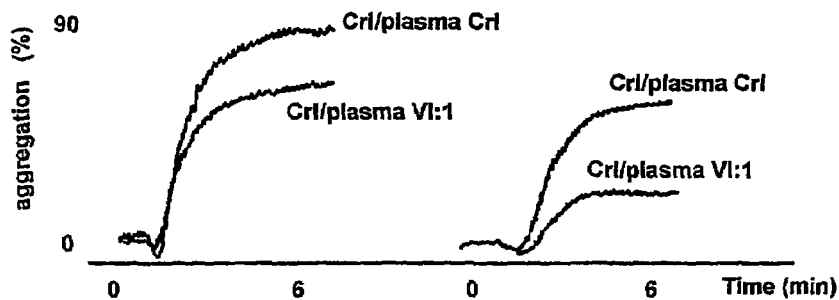

However, western blot analysis showed that platelets express the VPAC1 receptor. The active peptide PACAP (1-38) is mainly expressed in testis and brain but this peptide can cross the blood-brain barrier and is stably transported in plasma through coupling with ceruloplasmin (Banks W A, *J Pharmacol Exp Ther* (1993) 267: 690-696; Tams J W, *Biochem J* (1999) 341: 271-2768,9). PACAP is expressed in the human megakaryocytic cell lines MEG-01, DAMI and K562 and a rather weak expression was found in control platelets by RT-PCR (FIG. 3B). Western blot analysis further revealed that platelets express the VPAC1 receptor, the levels of which were normal in the patient (FIG. 3C). PACAP(1-38) was detected in human plasma by ELISA and significantly higher levels were found in patients VI:1 and V:4, and moderately increased levels in IV:5 and V:3, in contrast to a plasma pool of unrelated controls or IV:6 (FIG. 3D). Platelet aggregation using washed control platelets resuspended in citrated plasma from a control or patient VI:1, indicated that plasma from VI:1 inhibits the collagen induced aggregation (FIG. 3D). This could be due to the increased amount of PACAP(1-38) in this plasma.

D: Role for PACAP in Platelet Agqregation

Figure 4:
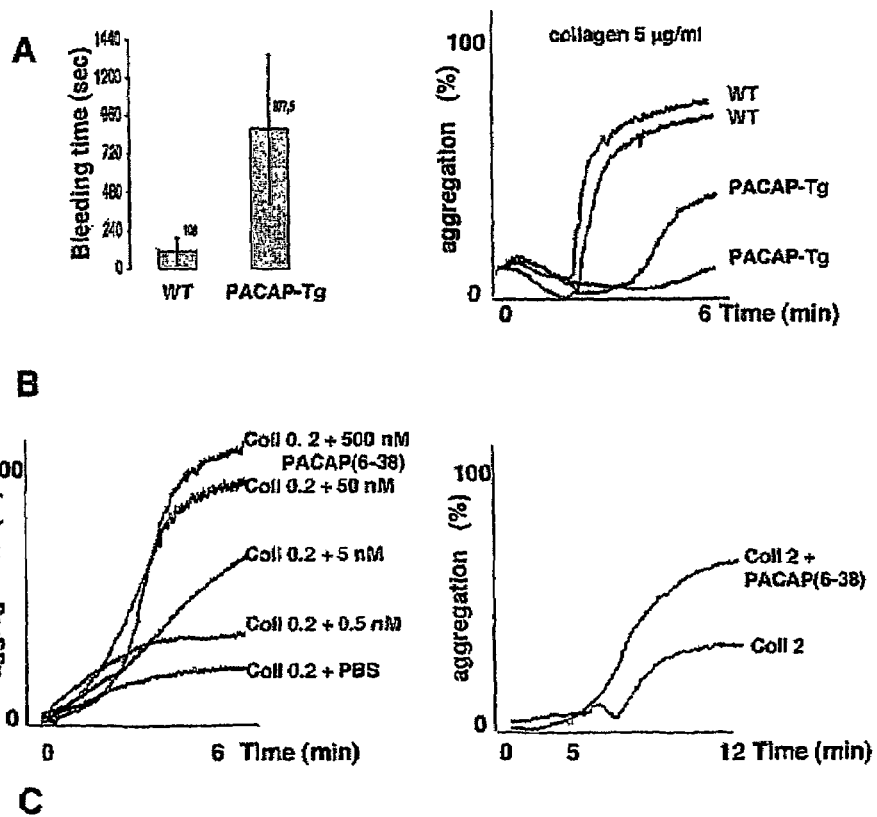
FIG. 4. Role of PACAP(6-38) in Platelet Aggregation.
Figure 4:
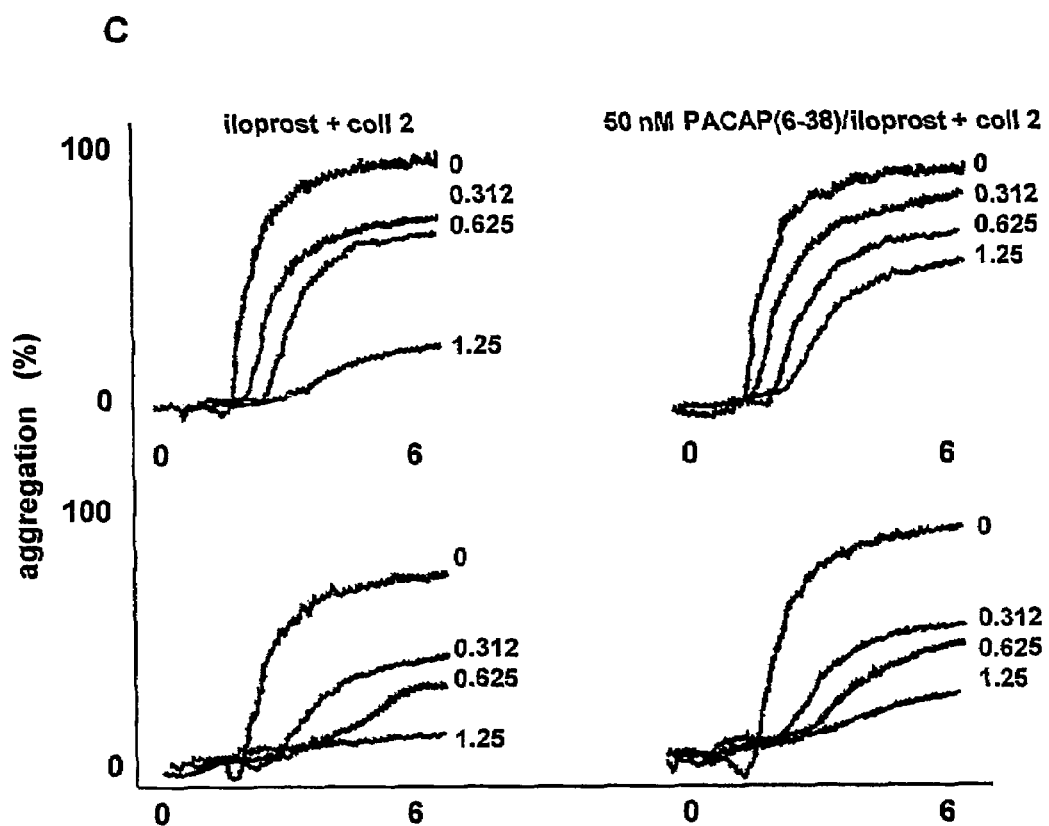

To establish the role of circulating PACAP(1-38) as a physiological inhibitor of collagen-induced platelet aggregation, various approaches were taken using different models. We made transgenic mice with a PACAP overexpression in the megakaryocyte lineage. As for the patients, these mice presented with an increased bleeding time and showed a decreased sensitivity towards collagen-induced aggregation (FIG. 4A). In another set of experiments, the patient phenotype was reversed, i.e. the activity of PACAP was neutralized by addition of the PACAP antagonist PACAP(6-38). This recombinant peptide has a 10-100 times higher affinity for the VPAC1 receptor than PACAP(1-38) but seems not to activate adenylyl cyclase (Vaudry et al., (2000) cited supra). PACAP (6-38) enhanced the collagen-induced aggregation of normal human platelets in a dose-dependent manner (FIG. 4B) and decreased basal cAMP levels (data not shown). The PACAP antagonist also induced a partial but consistent improvement of the collagen-induced platelet aggregation in the patient (FIG. 4B).

The functional platelet aggregation inhibition test for a control person in the presence of PACAP (6-38) results in a Gs loss-of-function (FIG. 4B). The influence of PACAP(6-38) on the platelet aggregation test for patient VI:1 was not that pronounced, probably because his PACAP plasma levels were too high.

Example 3

Influence of PACAP in Platelet Aggregation by Studies in Mice

Functional platelet studies from patient VI:1 show that increased levels of PACAP(1-38) in plasma result in increased basal cAMP levels and a platelet hypofunction. The role of PACAP(1-38) in platelet function was also studied in mice by subcutaneous injection of polyclonal or monoclonal anti-PACAP antibodies.

FVB mice were injected three times subcutaneously with 200 mg of an anti-PACAP or a control anti-b2-glycoprotein I polyclonal antibody or four times with 50 mg of an anti-PACAP (PP1A4) or an anti-RGS2 monoclonal antibody with an interval of 3 days between injections. At day 14 after the first injection, whole blood from the inferior vena cava of mice anesthetized by intraperitoneal injection of 60 mg/kg sodium pentobarbital was drawn into 20 µg/mL hirudin. A platelet count was performed on the venous blood sample using the Cell Dyne 1300 (Abbott). Blood was centrifuged at 100 g for 10 min, allowing separation of PRP, and PPP was obtained by centrifugation of the remaining blood at 2,000 g for 10 min. PRP and PPP were pooled from 5 mice in each group. Platelet aggregation was measured as described above with the platelet count adjusted to $250 \times 10^9$ platelets/L.

The antibodies had a similar effect on platelet aggregation as the PACAP antagonist PACAP(6-38). Platelets incubated with anti-PACAP antibodies (10 µm/ml) show an enhanced response towards collagen stimulation (FIG. 5). Moreover, when mice were functionally tested by platelet aggregation 7 days after their last injection, mice treated with anti-PACAP antibodies show the opposite phenotype to that observed in patient VI:1. In contrast to the treatment with the aspecific antibody against $O_2$-glycoprotein 1, anti-PACAP-treated mice show a weaker response towards activation of the Gs pathway and have an enhanced response towards collagen stimulation (FIGS. 5A,B).

Example 4

Influence of PACAP in Thrombocytopenia

Functional platelet studies on patient VI:1 show that increased levels of PACAP(1-38) result in increased basal platelet cAMP levels and platelet hypofunction. Since this patient also was thrombocytopenic, we have investigated whether elevated PACAP(1-38) would be associated with defective platelet formation. Platelets from this patient are smaller as the mean platelet volume (MPV) was 8.2 fL (normal MPV: 9-13 fL) and FACS analysis of his platelets showed a reduced expression of glycoprotein IX (FIG. 5D). Morphological examination of the bone marrow from the patient revealed a moderate to normal presence of the megakaryocyte lineage, indicative also of a normal proliferation. Electron microscopy of 2.5% glutaraldehyde fixed and routinely prepared ultrathin sections showed the presence of megakaryocyte progenitors but no mature megakaryocytes. The immature megakaryoblasts seemed to have reduced levels of rough endoplasmic reticulum cisternae and free ribosomes (FIG. 5E). Clear demarcation membranes were not seen. Specific granules as well as some dense core vesicles were obvious. Bone marrow from PACAP overexpressing and control mice was grown for 11 days in the presence of TPO, IL-6, IL-1b and SCF (Blair et al. (20022) *Br. J. Haematol.* 116:912-919.); FACS analysis showed a reduced expression of glycoprotein IIIa in megakaryocytes from the transgenic animals (FIG. 5D), indicative of a maturation defect. Transgenic mice present with a normal platelet count but their platelets have reduced levels of glycoprotein IIb/IIIa.

The role of PACAP(1-38) in thrombopoiesis was therefore further studied in control mice by subcutaneous injection of neutralizing polyclonal or monoclonal anti-PACAP antibodies. Mouse platelet-rich-plasma incubated with anti-PACAP antibodies in vitro (10 mg/ml) show an enhanced response towards collagen (data not shown), similar to the findings with the PACAP antagonist PACAP(6-38) using human platelets (FIG. 4B). Moreover, 7 days after, the last injection, anti-PACAP antibody treated mice show an enhanced response towards collagen ex vivo (FIG. 5B). Mice injected with the anti-PACAP polyclonal antibodies (n=5) furthermore have increased platelet numbers in comparison to the control group (n=5) ($1194 \pm 237 \times 109$ plt/L versus $722 \pm 178 \times 109$ plt/L, p=0.01-unpaired T-test) 14 days after the first injection. This experiment was repeated determining platelet numbers at different time points (days 0, 3, 7, 9, and 14), via tail bleeding (FIG. 5F). Mice injected with anti-PACAP polyclonal antibodies already showed increased platelet numbers 3 days after antibody injection.

The increased thrombocytopoiesis after pre-treatment with a polyclonal anti-PACAP antibody was studied under conditions of chemically suppressed bone marrow by the agent busulfan. This was done by subcutaneous injection of mice with either a polyclonal anti-PACAP or a control polyclonal antibody (at days 0, 3, and 7) and afterwards an intraperitonal injection of Busulfan (20 mg/kg) (at days 8 and 11). The platelet number was counted at different time points. Mice pretreated with, the polyclonal anti-PACAP antibody recovered more rapidly from their thrombocytopenic condition than the mice injected with the control antibody (FIGS. 8A,B).

Example 5

Generation of Polyclonal and Monoclonal Antibodies

The generation of monoclonal antibodies is exemplified in extenso for PACAP (1-38). The same methodology can be used for shorter versions of PACAP (n terminally or c terminally truncated). The same methodology can also be used for a full length PACAP receptor or for a fragment thereof. Preferred fragments of a PACAP receptor are the extracellular domains of these receptors.

A recombinant human PACAP(1-38) fusion protein, consisting of the amino acids encoded by the PACAP(1-38) peptide coupled to Glutathione S-transferase (GST) was expressed in *Eschedchia coli* and purified by affinity chromatography on immobilized glutathione (Amersham Biosciences). Recombinant human PACAP(1-38) is mixed with an equal amount of an adjuvant, and an obtained mixture is than subcutaneously administrated to Balb/c male mice (8 weeks old upon the start of immunization) in an amount corresponding to an amount of PACAP(i-38) of 100 μg per 1 mouse (priming immunization). After about 21 days, immunization can be performed by subcutaneous administration in the same manner as described above (booster immunization). After 19 days or 30 days from the booster, the mice can administrated through their tail veins with 200 μl of a preparation obtained by diluting human PACAP(1-38) with PBS (phosphate-buffered physiological saline) to have a concentration of 250 μg/ml (final immunization). Spleens have than to be excised from the mice after about 3 days from the final immunization, add they have to be separated into single cells. Subsequently, the spleen cells should be washed with a proper medium, e.g. DMEM medium. On the other hand, suitable mouse myeloma cells (e.g. Sp2/0-Ag14) have to be collected in the logarithmic growth phase, and to be washed with a proper medium, e.g. DMEM medium. The spleen cells and the mouse myeloma cells have to be sufficiently mixed in a plastic-tube in a ratio of numbers of the cells of 10:1, followed by addition of 50% (w/v) polyethylene glycol (PEG e.g. of Boehringer Mannheim, average molecular weight: 4000) to perform cell fusion at 37° C. for 7 minutes. After removal of the supernatant solution (by means of centrifugation), the residue is added with HAT medium (DMEM medium containing 10% fetal bovine serum added with hypoxanthine, aminopterin, and thymidine). The residue has to be suspended so that a concentration of the spleen cells of about $5 \times 10^6$ cells/ml is obtained. This cell suspension can than be dispensed and poured into 96-well plastic plates so that one well contains about 100 μl of the suspension, followed by cultivation at 37° C. in 5% carbon dioxide. HAT medium has to be supplemented; for instance in an amount of 50 μl/well on 2nd and 5th days. After that, half volume of the medium can be exchanged every 3 or 4 days in conformity with proliferation of hybridomas.

Screening and Cloning of Hybridomas: Hybridomas, which produce the monoclonal antibody of the present invention, have to be screened for. This has to be done by using, as an index, the inhibitory activity of the monoclonal antibody on the physiological activity possessed by PACAP. Hybridomas, which produced monoclonal antibodies exhibiting reactivity with PACAP's have then to be selected from the selected clones. The obtained hybridomas have then to be transferred to a suitable medium for instance HT medium which is the same as HAT medium except that aminopterin is removed from HAT medium, and cultured further. Cloning can be performed twice in accordance with the limiting dilution method by which stable hybridomas are obtainable.

Production and Purification of Monoclonal Antibodies: 2.6,10,14-Tetramethylpentadecane (e.g. Pristane of Sigma, 0.5 ml) can be intraperitoneally injected into Balb/c female mice (6 to 8 weeks old from the birth). After 10 to 20 days, cells of clones can be ($1 \times 10^6$ to 10 cells) suspended in PBS and intraperitoneally inoculated into the mice. After 7 to 10 days, the mice can be sacrificed and subjected to an abdominal operation, from which produced ascitic fluid can be collected. The ascitic fluid can be centrifuged to remove insoluble matters, and a supernatant was recovered and stored at −20° C. until purification Consequently, IgG can be purified from the ascitic fluid supernatant described above by using Hi-Trap Protein-A antibody purification kit (available from Pharmacia, Roosendaal, Netherlands). Namely, the ascitic fluid (2 ml) can be added with Solution A (1.5 M glycine, 3 M NaCl, pH 8.9, 8 ml), and filtrated with a filter for filtration having a pore size of 45 μm (Millipore). After that, an obtained filtrate can applied to a column (column volume: 1 ml) charged with Protein Sepharose HP (produced by Pharmacia) sufficiently equilibrated with Solution A, and the column has be washed with Solution A in an amount of 10-fold column volume. Subsequently, an IgG fraction can be eluted with Solution B (0.1 M glycine, pH 2.8) in an amount of 10-fold column volume. The eluted IgG fraction can be dialyzed against PBS. The monoclonal antibodies can be determined for their IgG subclasses by using the purified antibodies obtained in the foregoing, by means of a commercially available subclass-determining kit (trade name: Mono Ab-ID EIA Kit A, produced by Zymed). This method is based on the ELISA method. The Inhibitory Activities of Monoclonal Antibodies can be tested for their possible stimulatory effect on collagen-induced (0.35 μg/ml) platelet aggregation of human or mouse platelets. A similar approach may be used for the preparation of monoclonal antibodies specific to VIP or to PACAP receptor VPAC1 or VPAC2 or fragments thereof. Such antibodies can be applied for dosing activating or inhibitory PACAP mimetics by ELISA, for the purpose of monitoring PACAP (analogues) concentrations in the plasma of treated subjects. The VPAC1 have been cloned (Harmar et al. (1998) *Pharmacol Rev.* 50: 265-270). The human VPAC1 receptor DNA has been characterised from a HT29 human colonic adenocarcinoma cell line library. Human VPAC1 receptor comprises 457 amino acids (Sreedharan et al., (1993) *Proc. Natl. Acad. Scd. USA* 92: 2939-2943). The human VPAC1 receptor gene is located on region p22 of chromosome 3 (Sreedharan et al. (1995) *Biochem Biophys Res Commun* 193: 546-553). Cell lines, such *Saccharomyces cerevisae*, which are naturally devoid of VPAC1, can be transfected to produce such (Hansen M K (1999) *Receptors Chan-*

*nels* 6: 271-281). Vectors for expression of a PACAP receptor have been described in WO0107478. The method for preparation of a PACAP receptor protein has been disclosed in patent application US20020155533.

Preparation of F(ab)$_2$ or monovalent Fab fragments: In order to prepare F(ab')2 fragments, the monoclonal antibody can be dialyzed overnight against a 0.1 mol/L citrate buffer (pH 3.5). The antibody (200 parts) are then digested by incubation with pepsin (1 part) available from Sigma (Saint-Louis, Mo.) for 1:hour at 37° C. Digestion is consequently stopped by adding 1 volume of a 1 M Tris HCl buffer (pH 9) to 10 volumes of antibody. Monovalent Fab fragments can prepared by papain digestion as follows: a 1 volume of a 1M phosphate buffer (pH 7.3) is added to 10 volumes of the monoclonal antibody, then 1 volume papain (Sigma) is added to 25 volumes of the phosphate buffer containing monoclonal antibody, 10 mmol/l L-Cysteine HCl (Sigma) and 15 mmol/L ethylene diaminetetra-acetic acid (hereinafter referred to as EDTA). After incubation for 3 hours at 37° C., digestion is stopped by adding a final concentration of 30 mmol/l freshly prepared iodoacetamide solution (Sigma), keeping the mixture in the dark room temperature for 30 minutes. Both F(ab')2 and Fab fragments can further be purified from contaminating intact IgG and Fc fragments using protein-A-Sepharose. The purified fragments can finally dialyzed against phosphate-buffered saline (herein after referred as PBS). Purity of the fragments can be determined by sodium-dodecylsulphate polyacrylamide gel electrophoresis and the protein concentration can be measured using the bicinchonicic acid Protein Assay Reagent A (Pierce, Rockford, Ill.).

The invention claimed is:

1. A method of treating thrombocytopenia in a subject having thrombocytopenia, said method comprising the step of administering to said subject a compound inhibiting PACAP activity, wherein said compound inhibiting PACAP activity is a neutralizing anti-PACAP antibody or an antigen-binding fragment thereof.

2. The method of claim 1, wherein said neutralizing antibody or antigen binding fragment inhibits mature PACAP or an isoform thereof.

3. The method according to claim 1, wherein said thrombocytopenia is infection-induced thrombocytopenia or treatment-induced thrombocytopenia.

4. The method according to claim 1 wherein said neutralizing anti-PACAP antibody or antigen-binding fragment thereof, is capable of binding to the PACAP(1-38) polypeptide consisting of the amino acid sequence of SEQ ID NO:1.

5. A method of lowering the risk of acquiring or developing thrombocytopenia in a subject having a high probability of acquiring or developing thrombocytopenia, said method comprising the step of administering to said subject a compound inhibiting PACAP activity wherein said compound inhibiting PACAP activity is a neutralizing anti-PACAP antibody or an antigen-binding fragment thereof.

6. The method according to claim 5, wherein said subject has cancer and wherein said compound is adminstered prior or during chemotherapy.

7. The method according to claim 5, wherein said subject is at risk of developing infection-induced thrombocytopenia.

* * * * *

UNITED STATES PATENT AND TRADEMARK OFFICE
CERTIFICATE OF CORRECTION

| | | |
|---|---|---|
| PATENT NO. | : 7,615,219 B2 | Page 1 of 1 |
| APPLICATION NO. | : 10/542238 | |
| DATED | : November 10, 2009 | |
| INVENTOR(S) | : Freson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 782 days.

Signed and Sealed this
Fifteenth Day of March, 2011

David J. Kappos
*Director of the United States Patent and Trademark Office*